United States Patent [19]

Ananthapadmanabhan et al.

[11] Patent Number: 4,738,925

[45] Date of Patent: Apr. 19, 1988

[54] METHOD OF INCREASING SOLUBILITY OF ENZYMES

[75] Inventors: Kavssery P. Ananthapadmanabhan, Spring Valley, N.Y.; Errol D. Goddard, Haworth, N.J.

[73] Assignee: Union Carbide Corporation, Danbury, Conn.

[21] Appl. No.: 728,243

[22] Filed: Apr. 29, 1985

[51] Int. Cl.[4] .......................... C12N 9/56; C12N 9/00; C12N 9/50; C12N 9/54; C12N 9/52
[52] U.S. Cl. .................................... 435/222; 435/183; 435/219; 435/212; 435/213; 435/226; 435/227; 435/229; 435/230; 435/816; 435/220
[58] Field of Search ........ 435/183, 212, 213, 219–230, 435/814, 816; 252/174.12

[56] References Cited

U.S. PATENT DOCUMENTS

| | | | |
|---|---|---|---|
| 4,144,130 | 3/1979 | Kula et al. | 435/210 X |
| 4,515,705 | 5/1985 | Moeddel | 252/174.12 |

OTHER PUBLICATIONS

Biochemistry, vol. 12, No. 13, 1973, pp. 2525–2530.

*Primary Examiner*—Lionel M. Shapiro
*Attorney, Agent, or Firm*—Steven H. Flynn

[57] ABSTRACT

A method is provided for increasing the solubility of an enzyme in an aqueous solution comprising providing a water-soluble anionic surfactant to the solution and further providing the solution with a pH above that which result in the formation of an enzyme/surfactant precipitate. The application is further directed to an aqueous solution containing an anionic surfactant and having an enzyme concentration contained therein which is higher than that possible in the absence of the surfactant.

9 Claims, No Drawings

METHOD OF INCREASING SOLUBILITY OF ENZYMES

This invention relates to an improved process for the recovery of enzymes from solution through increasing the solubility of the enzyme. In particularly advantageous aspects, the instant invention relates to an improved process for the recovery of enzymes through the use of a two-phase aqueous system wherein the solubility of the enzyme in at least one phase is increased.

BACKGROUND OF THE INVENTION

The potential applications for biologically active proteins have greatly increased. Commercial implementation of this technology now frequently depends on the ability to isolate these substances at reasonable cost. Until recently, separation technology which could support industrial applications was limited to filtration and centrifugation. However, these techniques are extremely dependant upon particle size and therefore approach their limit of usefulness during the harvest of even small intact microorganisms. The problems encountered are therefore greatly increased during the attempted isolation of intracellular components from ruptured cells where component size is, of course, greatly reduced.

The process of affinity partitioning using two phase aqueous systems has been suggested for some separations. Affinity partitioning basically involves the formation of multiple, distinct phases in a common solvent following the addition of materials, such as polymers, which produce immiscible phases when in solution and the selective affinity of a molecule for one phase over the other.

Aqueous two phase systems have been known since the late nineteenth century from the work of Beijernick who published his findings regarding aqueous phase formation with agar and gelatin. As affinity partitioning is not dependant upon particle size as are conventional techniques such as filtration and centrifugation, it offers the potential of improved recovery of cellular components in industrial scale recoveries. The use of affinity partitioning in the isolation of enzymes from other cellular matter is disclosed in U.S. Pat. No. 4,144,130. Affinity partitioning technology has further been employed to date in the recovery of interferon (U.S. Pat. No. 4,343,735), the isolation of human coagulation factors VII and VIIa (U.S. Pat. No. 4,470,969) and the isolation of deoxyribonucleic acid (U.S. Pat. No. 4,207,200).

Alkaline Protease

Alkaline proteases are members of a class of enzymes which demonstrate peak proteolytic activity under neutral to alkaline conditions.

Alkaline proteases are known to possess excellent cleansing performance against proteinaceous substances found, for example, in clothing stains, especially when employed in the presence of a cleansing agent, such as a detergent, under alkaline conditions. Proteases are therefore attractive additives for cleansing formulations.

Enzymes, like other compounds, exhibit an upper limit of solubility in a given medium. The addition of enzyme above this amount results only in its precipitation. However, unlike some compounds, enzymes are highly sensitive to their environment. Therefore, some conventional solubility-increasing techniques which may be employed with compounds other than enzymes may not be used with enzymes. For example, elevating the temperature of an enzyme-containing solution in an effort to increase its solubility is limited by the temperature at which the enzyme will denature, thereby losing its activity. Such efforts are further energy insensitive and therefore economically unattractive.

Therefore, processes for enzyme recovery which rely upon enzyme solubility, such as affinity partitioning, are restricted in their utility as the recovery of an enzyme in great quantities requires a correspondingly large volume of solvent. Further economic considerations, such as ease of storage and transportation, often require the concentration of an enzyme-containing solution through removal of a portion of the solvent. This procedure is also limited by enzyme solubility.

The applicant has therefore sought to provide through the present invention an improved method for isolation and recovery of an enzyme through its increased solubility in an aqueous medium, and the solution produced thereby. Applicant has further sought to provide an improved process for the recovery of enzymes through the use of a two-phase aqueous system wherein the solubility of the enzyme in at least one phase is increased. Applicant has further sought to accomplish the above without significantly degrading the activity of the enzymes.

In a particularly advantageous aspect of the present invention, applicant has provided for improved yields of alkaline protease through the use of an affinity partitioning process. Applicant has further provided a solution of improved solubility to alkaline protease.

SUMMARY OF THE INVENTION

The present invention is directed to a method increasing the solubility of an enzyme in an aqueous solution comprising adding an anionic surfactant to the enzyme-containing solution and providing the solution with a pH above that which results in the formation of an enzyme/surfactant precipitate.

The present invention is further directed to a method of producing an enzyme-containing aqueous solution comprising
a. introducing at least one enzyme into a two phase aqueous system containing an anionic surfactant;
b. providing said aqueous system with a pH greater than that of the isoelectric point of said at least one enzyme;
c. removing the enzyme rich phase of said aqueous system.

The present invention further relates to a composition comprising water, an anionic surfactant and an enzyme, said solution having a pH above that which would cause the formation of an enzyme/surfactant precipitate.

DETAILED DESCRIPTION OF THE INVENTION

The methods of the invention may generally be applied in the isolation and recovery of enzymes from an aqueous solution.

The preferred enzymes include proteolytic enzymes, which are those enzymes which hydrolyze —CO—NH— linkages. These include exopeptidases, which selectively act upon terminal amino groups of a peptide chain, and endopeptidases, which are indiscriminant in the location of their action, and mixtures thereof. They may originate from plants, animals or procaryotic or eucaryotic microbes. Representative of individual species of proteolytic enzymes include alkaline protease, pepsin, renin, trysin, chymotrypsin, pankrin enterokinase, papain, chymopapain, ficin, bromelin, B. subtilis proteinase, insulinase, Aspergillus proteinase, carboxypeptidase, protaminase, asparaginase, fungal penicillin amidase, bacterial penicillinase and mixtures thereof. Commercially available alkaline proteases include Alkalase manufactured by Novo and the Milezyme APL series, manufactured by Miles Laboratories.

The procedures claimed herein are also applicable to the isolation of enzymes from aqueous solutions containing intact cells or fragments thereof. The process of affinity partitioning, discussed below, may therefore be employed to isolate the enzyme directly from the enzyme-containing phase of the multi-phase system, thereby consolidating enzyme isolation and preparation of the claimed composition.

The surfactants useful in the present invention are anionic. Representative of anionic surfactants are sodium $C_8$–$C_{18}$ alkyl sulfates, potassium $C_8$–$C_{18}$ alkyl sulfates, sodium $C_8$–$C_{18}$ alkyl suulfonates, potassium $C_8$–$C_{18}$ alkyl sulfonates, sodium $C_9$–$C_{15}$ alkylbenzene sulfonates, potassium $C_9$–$C_{15}$ alkylbenzene sulfonates, sodium alkyl glyceryl ether sulfonates, sodium coconut oil fatty acid monoglyceride sulfonates, sodium coconut oil fatty acid monoglyceride sulfates, sodium salts of $C_8$–$C_{12}$ alkyl phenol ethylene oxide ether sulfates containing from about 1 to about 10 units of ethylene oxide per molecule, potassium salts of $C_8$–$C_{12}$ alkyl phenol ethylene oxide ether sulfates containing from about 1 to about 10 units of ethylene oxide per molecule, sodium salts of $C_{10}$–$C_{20}$ alkyl ethylene oxide ether sulfates containing from about 1 to about 10 units of ethylene oxide per molecule, potassium salts of $C_{10}$–$C_{20}$ alkyl ethylene oxide ether sulfates containing from about 1 to about 10 units of ethylene oxide per molecule, water-soluble salts of esters of alpha-sulfonated fatty acids containing about 6 to 20 carbon atoms in the fatty acid group and from about 1 to 10 carbon atoms in the ester group, water-soluble salts of 2-acyoxy-alkane-1-sulfonic acids containing from about 2 to about 9 carbon atoms in the acyl group and from about 9 to about 23 carbon atoms in the alkane moiety, alkyl ether sulfates containing from about 10 to 20 carbon atoms in the alkyl group and from about 1 to 30 moles of ethylene oxide, water-soluble salts of olefin sulfonates containing from about 12 to 24 carbon atoms, beta-alkyloxy- alkane sulfonates containing about 1 t 3 carbon atoms in the alkyl group and from about 8 to 20 carbon atoms in the alkane moiety, alkali metal soaps of higher fatty acids containing from about 8 to about 24 carbon atoms, and mixtures thereof. Preferred are sodium dodecylsulfate and soldium dodecyl benzene sulfonate.

The anionic surfactants should be present in amounts ranging up to about 30 wt. % based on the total weight of the solution. More preferably, the anionic surfactants should be present in amounts ranging up to about 5 wt. % based on the total weight of the solution. Most preferably, sodium dodecylsulfate and the soldium dodecyl benzene sulfonate is present in amounts up to about 3 wt. % based on the total weight of the system.

The pH of the solution should be maintained at a level above that which would cause the formation of an enzyme/surfactant precipitate. This will, of course, vary with the enzyme. Preferably, the pH should be maintained above the isoelectric point of the enzyme which is that point at which the enzyme bears no net electrostatic charge. The isoelectric point may be determined with gel electrophoresis and is characterized by the absence of migration by the enzyme to either electrode. The preferred alkaline protease enzyme has an isoelectric point in the reange of about 7 to 9.

Other reaction conditions are not critical with the proviso that those employed do not denature the enzyme. For example, in the case of the preferred enzyme, alkaline protease, temperatures should be maintained below about 70 degrees Celsius.

In addition to the aforementioned reaction components, the system may further contain additional water-soluble adjuvants, such as polyethylene glycol and copolymers of ethylene oxide and propylene oxide. The adjuvants may be present in amounts up to about 50 wt. % based on the total solution. Preferably, the adjuvant is polyethylene glycol. Most preferably, the adjuvant is polyethylene glycol having an average molecular weight of from about 1,000 to about 10,000. In the case of this most preferred adjuvant, it is present in amounts of from about 5 to about 50 wt. %, more preferably about 5 to about 30 wt. % based on the weight of the total solution. The adjuvants may be added or may already be present as in the case of polyethylene glycol as a common ingredient in the establishment of the aqueous two-phase systems commonly emloyed in affinity partitioning processes.

As previously mentioned, the process of affinity partitioning may be used for the production of an aqueous, enzyme-containing phase to which the claimed methods may be emloyed. In affinity partitioning, an aqueous system having at least two phases is employed. A number of systems suitable for the separation of enzymes, such as proteases, are known, for instance those described in Albertsson, P. A., *Partition of Cell Particles and Macromolecules*, Uppsala, 1st edition (1960), 2nd edition (1971) and U.S. Pat. No. 3,897,414.

Examples of two phase aqueous systems which have been used in the isolation of biological matter and containing at least two polymers are: dextran/water-soluble copolymer of sucrose and epichlorohydrin, dextran/hydroxypropyl-dextran, polyethylene glycol/dextran sulphate, charged polyethylene glycol/dextran,dextran/ polyethylene glycol, polypropylene glycol/methoxypolyethylene glycol, polypropyleneglycol/polyethylene glycol, polypropylene glycol/polyvinyl alcohol, polypropylene glycol/ polyvinyl pyrrolidone, polypropylene glycol/hydroxypropyldextran, polypropylene glycol/dextran, polyethylene glycol/polyvinyl alcohol, polyethylene glycol/polyvinyl pyrrolidone, polyethylene glycol/water-soluble copolymer of sucrose and epichlorohydrin, polyethylene glycol/water-soluble starch, polyethylene glycol/glycogen, polyvinyl alcohol/methyl cellulose, polyvinyl alcohol/hydroxypropyl-dextran, polyvinyl alcohol/dextran, polyvinyl pyrrolidone/methyl cellulose, polyvinyl pyrrolidone/- dextran, methyl cellulose/hydroxypropyl dextran, methyl cellulose/dextran and ethylhydroxyethyl cellulose/dextran. These aqueous systems may also contain additional salts and organic solvents, adjuvants, etc.

Other aqueous systems which have been used in the isolation of these materials are those composed of at least one polymer and one salt or organic solvent. The polymers may be chosen from those listed immediately above and is preferably polyethylene glycol, polypropylene glycol, polyvinyl pyrrolidone or a polysaccharide or a water-soluble derivative thereof. Representative examples of salts are magnesium sulfate, potassium sulfate and sodium chloride. The organic solvents may include propylalcohol, glycerol and 2-butoxyethanol.

The systems can further contain additional materials including pH buffers such as tris(hydroxymethyl)aminomethane, morpholino ethane sulfonate and citrate, which may be emloyed with saline.

The enzyme-containing aqueous phase may be removed from the partitioning sytem and further treated as desired.

The following examples illustrate embodiments of the present invention and are not to be construed as a limitation of its scope.

These examples are offered to demonstrate the improved recovery of an enzyme from solution as demonstrated the enzymatic activity of the solution.

All parts and percentages are by weight unless otherwise indicated. All temperature values are given in degrees Celsius.

EXAMPLES

Control

A liquid alkaline protease-containing composition manufactured by Miles Laboratories and marketed under the designation APL 440 was used in the following examples. According to its manufacturer, APL 440 possesses an activity of approximately 440,000 DAPU/g. A DAPU, or Detergent Alkaline Protease Unit, is defined as that activity which will liberate four nanomoles of tyrosine per minute under specified conditions. The method employed in the determination of this activity will be set forth below. The alkaline protease content of APL 440 is not known. Therefore, for the purposes of the following experiments, APL 440 is assumed to be 100% pure and its activity is assumed to be 440,000 DAPU/g.

Determination of Activity

In the experiments presented below, the determination of enzymatic activity is based on a proteolytic hydrolysis of a Hammerstein casein substrate in synthetic tap water over a period of 40 minutes at 40 degrees Celsius. The synthetic tap water possesses a hardness of 269 ppm of calcium carbonate, a pH of 8.5. Unhydrolysed substrate is precipitated with trichloroacetic acid and removed by centrifugation. The solubilized casein is then determined spectrophotometrically.

The following stock solutions were prepared.

Sol. 1. 500 ml. distilled water containing 12.6 g. of calcium chloride dihydrate.

Sol. 2. 500 ml. distilled water containing 7.0 g. of magnesium chloride.

Sol. 3. 500 ml. distilled water containing 10.5 g of anhydrous sodium bicarbonate.

STW: Synthetic tap water prepared by introducing 10 ml. of each of solutions 1, 2 and 3 into 970 ml. of distilled water.

STPP: Sodium tripolyphosphate solution (2.0%) prepared by introducing 20 g. of sodium tripolyphosphate and 10 ml. of each of solutions 1, 2 and 3 into 970 ml. of distilled water with continuous agitation until completely dissolved. The pH of the solution was then adjusted to 8.5±/-0.1 using 0.1 N HCl. Any precipiate was allowed to settle but was not removed from the solution.

Sol. 4. 400 ml. distilled water containing 90.3 g of anhydrous sodium acetate diluted to 500 ml. with distiled water.

Sol. 5. 350 ml. distilled water containing 150 g of glacial acetic acid.

Sol. 6. 47.5 ml. of distilled water containing 2.5 ml. of polysorbate 80.

TCA: The trichloroacetic acid (TCA) reagent was prepared by mixing 18 g. of TCA with 100 ml. of each of Solutions 4 and 5 and 4 ml. of Solution 6. The resulting solution was then diluted to one liter with distilled water.

THAM: 400 ml. of STW containing 18.17 g. of tris-hydroxymethyl amino methane.

A casein-containing solution is then prepared by adding, under constant agitation, 6.67 g.(moisture free basis) of Hammerstein casein to 350 ml. of the STW solution. Stirring is then continued for ten minutes. 50 ml. of THAM solution is then added and stirring is again continued for 10 minutes. The resulting solution is then allowed to equilibrate in a water bath having a temperature of 40±/-0.1 degrees C. for 30 minutes. The pH of the solution is then adjusted to 8.5±/-0.1 at 40 degrees C. with 1N NaOH. The solution is allowed to cool to room temperature. It is then diluted to 500 ml. with STW solution. It should be noted that this solution must be prepared daily.

An enzyme-containing solution is then prepared in the STPP solution such that one ml. of the final dilution will have an activity of 20–40 DAPU/ml. The pH of the final dilution is adjusted to 8.5 using either 1N HCL or 1N NaOH.

A 5 ml. sample of the enzyme-containing solution is then transferred to a 25×150 mm. test tube and placed in a constant temperature water bath maintained at 40 degrees C. 5 ml. portions of the casein substrate are then pipetted into each of three 25×150 mm test tubes, one of which is to used as a standard for comparative purposes. These samples are then placed in the water bath and allowed to equilibrate at 40 degrees C. for 10 minutes.

Noting the exact time, 1 ml. of the enzyme solution is then introduced into two of the substrate-containing test tubes which are then stoppered. After exactly 40 minutes, 5 ml. of TCA solution is added to each tube and mixed by gentle swirling of the contents.

An enzyme blank is then prepared by adding 5 ml. of TCA solution into the remaining substrate-containing test tube and mixing its contents by gentle swirling.

All test tubes are then placed in the water bath and incubated for 30 minutes. After exactly 30 minutes have passed, the test tubes are transferred to an ice bath where they are allowed to remain for about 5 minutes. The tubes are then centrifuged at about 3000 rpm for about 15 minutes. The supenatant is then recovered into clean cuvettes. The adsorbance of UV radiation (275 nm) by each sample is recorded.

The absorbance data is then used to calculate the activity of the enzyme through the formula set forth immediately below.

$$DAPU/g = A \times 11/0.00552 \times 40 \times W$$

wherein A is absorbance difference between the enzyme/substrate sample and the enzyme blank, 11 is the final reaction volume, 0.00552 is the absorbance of 4 nanomoles of tyrosine, 40 is the elapsed time in minutes and W is the weight in grams added to the reaction mixture in one 1 ml. aliquot.

EXAMPLE 1

Approximately 1.0 gram of 100% APL 440 was placed in a 25×150 mm test tube to which was added a 50% solution of polyethylene glycol having an average molecular weight of 3350 and marketed by Union Carbide Corporation under the tradename Carbowax 3350. The vessel was hand shaken during the addition of the polyethylene glycol-containing solution. Addition of the polyethylene glycol-containing solution was ceased when turbidity of the solution resulted. While not wishing to be limited to a specific reaction mechanism, it is believed that through the addition of polyethylene glycol to the alkaline protease-containing solution, water once available for the dissolution of alkaline protease is bound up by the glycol. Therefore, at the point of turbidity, the solution was assumed to contain the minimum water capable of keeping the available enzyme in solution. However, it is also possible that the limited solubility is due to the formation of a polyethylene glycol/alkaline protease complex of low solubility.

Based upon the relative concentrations of the final solution's components and the activity of the solution, it was determined that the polyethylene glycol solution was capable of carrying 2,205,514 DAPU/kg of 100% polyethylene glycol.

EXAMPLE 2

The procedure of Example 1 was repeated except that prior to the addition of the polyethylene glycol solution, 0.2 grams of a 1.0% solution of sodium dodecylsulfonate was added to the test tube. The polyethylene glycol solution was then added until precipitation occurred.

Based upon the relative concentrations of the solution's components and the activity of the solution, it was determined that the polyethylene glycol solution was capable of carrying 4,426,559 DAPU/kg of 100% polyethylene glycol.

EXAMPLE 3

The procedure of Example 2 was duplicated except that only 0.1 gram of the surfactant was employed. The activity per gram of polyethylene glycol was in this case calculated to be 4,395,604 DAPU/kg of 100% polyethylene glycol.

EXAMPLE 4

The procedure of Example 2 was duplicated except that 0.1 grams of a 10.0% solution of the surfactant was employed. The activity per gram of polyethylene glycol was in this case calculated to be 2,205,513 DAPU/kg of 100% polyethylene glycol.

EXAMPLE 5

The procedure of Example 4 was duplicated except that 0.2 grams of a 10.0% solution of the surfactant was employed. The activity per gram of polyethylene glycol was in this case calculated to be 1,674,277 DAPU/kg of 100% polyethylene glycol.

EXAMPLE 6

The procedure of Example 4 was duplicated except that 0.3 grams of a 10.0% solution of the surfactant was employed. The activity per gram of polyethylene glycol was in this case calculated to be 1,102,756 DAPU/kg of 100% polyethylene glycol.

EXAMPLE 7

In order to demonstrate the retention of activity of the enzyme after contact with a surfactant, the following experiment was conducted.

A 20% solution of a polyethylene glycol having an average molecular weight of 3350 and marketed by Union Carbide Corporation under the name "Carbowax 3350" was prepared in distilled water. To 2.5 grams of this solution were added 0.9 g. of a 0.1% solution of APL 440 alkaline protease and 0.8 g. of a 0.1 % solution of sodium dodecylsulfate. The resulting solution was agitated and then tested for enzymatic activity as described above.

The solution was found to possess 98.9% of its original activity.

From the data set forth above, it can be clearly seen that an increased solubility of an enzyme in a solution can be accomplished through use of the instant invention. Furthermore, the activity of the enzyme appears not to be unduly affected by such treatment.

We claim:
1. A method for increasing the solubility of alkaline protease in an aqueous solution, said method comprising
  (a) introducing into said aqueous solution an anionic surfactant in quantities sufficient to increase the solubility of said enzyme in said aqueous solution, said surfactant being selected from the group consisting of sodium dodecylsulfate and sodium dodecyl benzene sulfonate; and
  (b) providing said aqueous solution with a pH above that which results in the formation of an alkaline protease/surfactant precipitate.
2. The method of claim 1 wherein the aqueous solution is provided with a pH of 7 to 9.
3. The method of claim 1 wherein the surfactant is present in an amount no greater than 3 wt. %, based upon the total weight of the solution.
4. The method of claim 1 wherein the anionic surfactant is present in an amount of up to 3 wt. % based on the total weight of the solution.
5. The method of claim 1 wherein the aqueous solution further contains a water-soluble adjuvant selected from the group consisting of polyethylene glycol and copolymers of ethylene oxide and propylene oxide.
6. The method of claim 5 wherein the adjuvant is present in an amount of from about 5 to 50 wt. % based on the total solution.
7. The method of claim 5 wherein the compound is polyethylene glycol.
8. The method of claim 7 wherein the polyethylene glycol has an average molecular weight of from about 1,000 to about 10,000.
9. The method of claim 8 wherein the polyethylene glycol is present in amounts of from about 5 to 30 wt. % based on the weight of the total solution.

* * * * *